US00PP37154P3

(12) United States Plant Patent
Beatson

(10) Patent No.: US PP37,154 P3
(45) Date of Patent: Dec. 16, 2025

(54) HOP PLANT NAMED 'NZH-2077'

(50) Latin Name: ***Humulus lupulus* L.**
Varietal Denomination: NZH-2077

(71) Applicant: NEW ZEALAND HOPS LIMITED, Nelson (NZ)

(72) Inventor: Ronald Alan Beatson, Motueka (NZ)

(73) Assignee: NEW ZEALAND HOPS LIMITED, Appleby (NZ)

( * ) Notice: Subject to any disclaimer, the term of this patent is extended or adjusted under 35 U.S.C. 154(b) by 0 days.

(21) Appl. No.: 19/195,755

(22) Filed: May 1, 2025

(65) Prior Publication Data

US 2025/0344619 P1 Nov. 6, 2025

Related U.S. Application Data

(60) Provisional application No. 63/642,029, filed on May 3, 2024.

(51) Int. Cl.
*A01H 5/02* (2018.01)
*A01H 6/28* (2018.01)

(52) U.S. Cl.
USPC ..... Plt./236
CPC ..... *A01H 6/28* (2018.05)

(58) Field of Classification Search
USPC ..... Plt./236
CPC ..... A01H 5/02
See application file for complete search history.

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

The new hop plant 'NZH-2077' is provided. The new plant was produced by crossing '05.L205-239' (the female parent, i.e., the seed parent; not patented) with a diploid male selection 'L13.008-004' (i.e., the pollen parent; not patented) in the course of a planned breeding program. 'NZH-2077' is characterized by having large, medium compact cones which are late season maturing.

3 Drawing Sheets

CROSS REFERENCE TO RELATED APPLICATIONS

This application claims priority to U.S. Provisional Patent Application No. 63/642,029, which was filed on May 3, 2024, the contents of which are hereby incorporated by reference for all purposes.

Latin name of genus and species of plant claimed: *Humulus lupulus* L.

Variety denomination: 'NZH-2077'.

BACKGROUND OF THE INVENTION

The new variety of hop, *Humulus lupulus* L., of the present invention was created in the course of a planned breeding program carried out at Motueka, New Zealand. It was selected from a population of triploid seedlings derived from crossing the diploid '05.L205-239' (the female parent, i.e., the seed parent; not patented) with a tetraploid male selection 'L13.008-004' (i.e., the pollen parent; not patented).

The parentage of the new variety can be summarized as follows:

'05.L205-239' x 'L13.008-004'

The cross was carried out in January 2015. The seeds resulting from the above cross were germinated and the seedlings were then raised and planted in a field at Motueka, New Zealand in November 2015. The seedlings remained in the field for the 2015-2016 and 2016-2017 seasons to allow for agronomic, sensory, and chemistry traits to be measured and/or assessed. Selective study resulted in the identification of a single plant of the new variety from the population of seedlings derived from the above cross.

During the 2019 season the new variety was clonally propagated using soft tip methods and 15 rooted cutting plants were potted. The resulting plants were found to be true to type demonstrating that the characteristics of the new variety are stable and strictly transmitted by asexual propagation from one generation to another.

Further plants of the new variety were asexually propagated and a trial plot was planted in 2021-2022.

SUMMARY OF THE INVENTION

It was found that the new variety of hop plant of the present invention is characterized by having large cones that are medium in compactness which are late season maturing.

The new variety can be readily distinguished from its ancestors. More specifically, the new variety is triploid whereas the seed parent, '05.L205-239', is a diploid and the pollen parent, 'L13.008-004', is a tetraploid. Moreover, the new variety of the present invention can readily be distinguished from other similar non- parental varieties. For example, when compared to 'Southern Cross' (not patented), the new variety has cones which mature late in the season, compared to 'Southern Cross' which has mid-season maturing cones. In addition, '85-03-06' (not patented) has small cones compared to the large cones of the new variety.

The new variety has been named 'NZH-2077'. The new variety was previously named L15.052-077. L15.052-077 has also been referred to as the Breeder Code for the new variety.

BRIEF DESCRIPTION OF THE DRAWINGS

The accompanying photographs show as nearly true as it is reasonably possible to make the same, in a color illustration of this character, typical specimens of the new variety. The illustrated plants were approximately three years old.

DETAILED BOTANICAL DESCRIPTION

Figure 1:
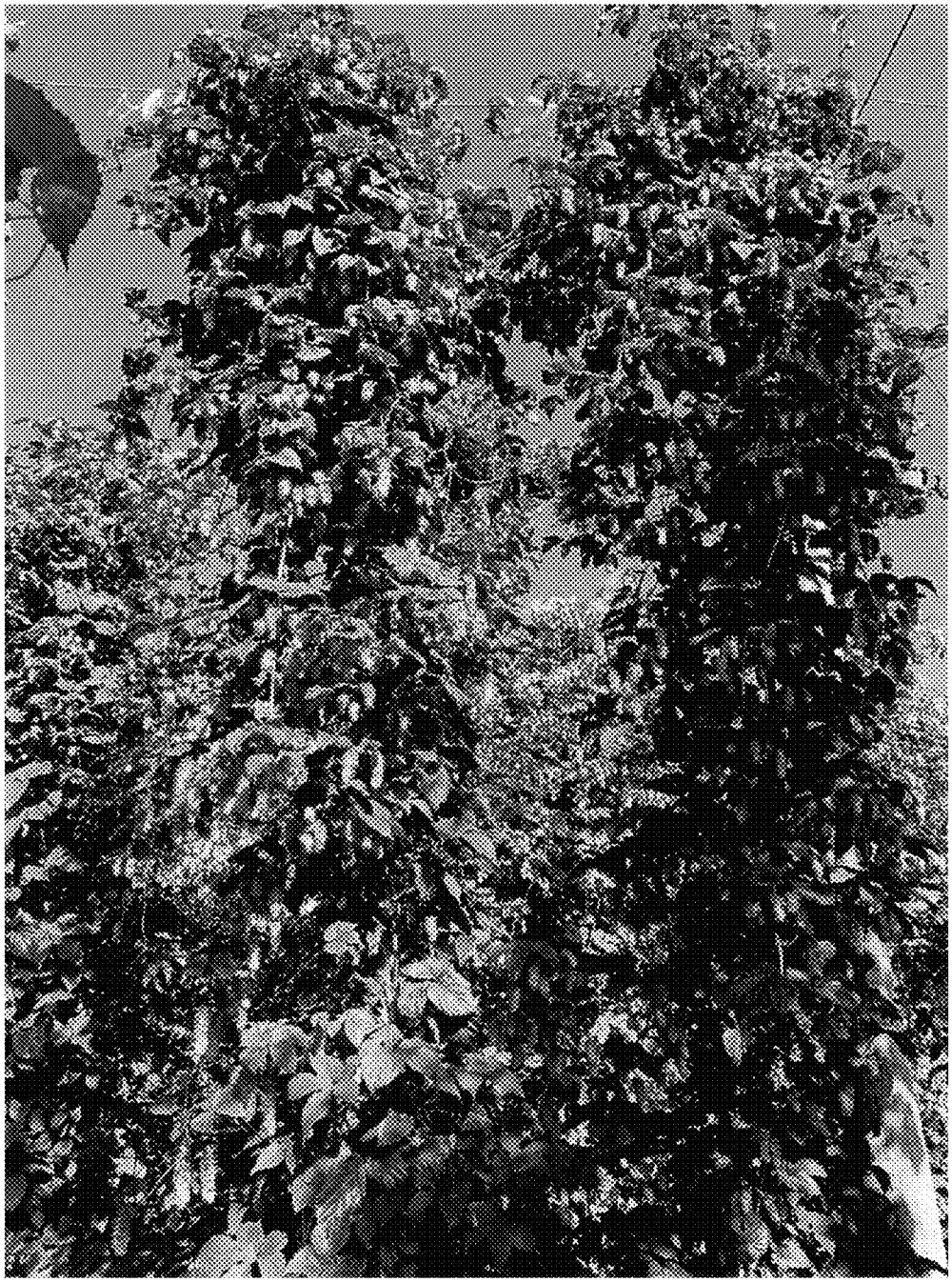
FIG. 1 illustrates a specimen of the 'NZH-2077' plant growing outdoors.
Figure 2:
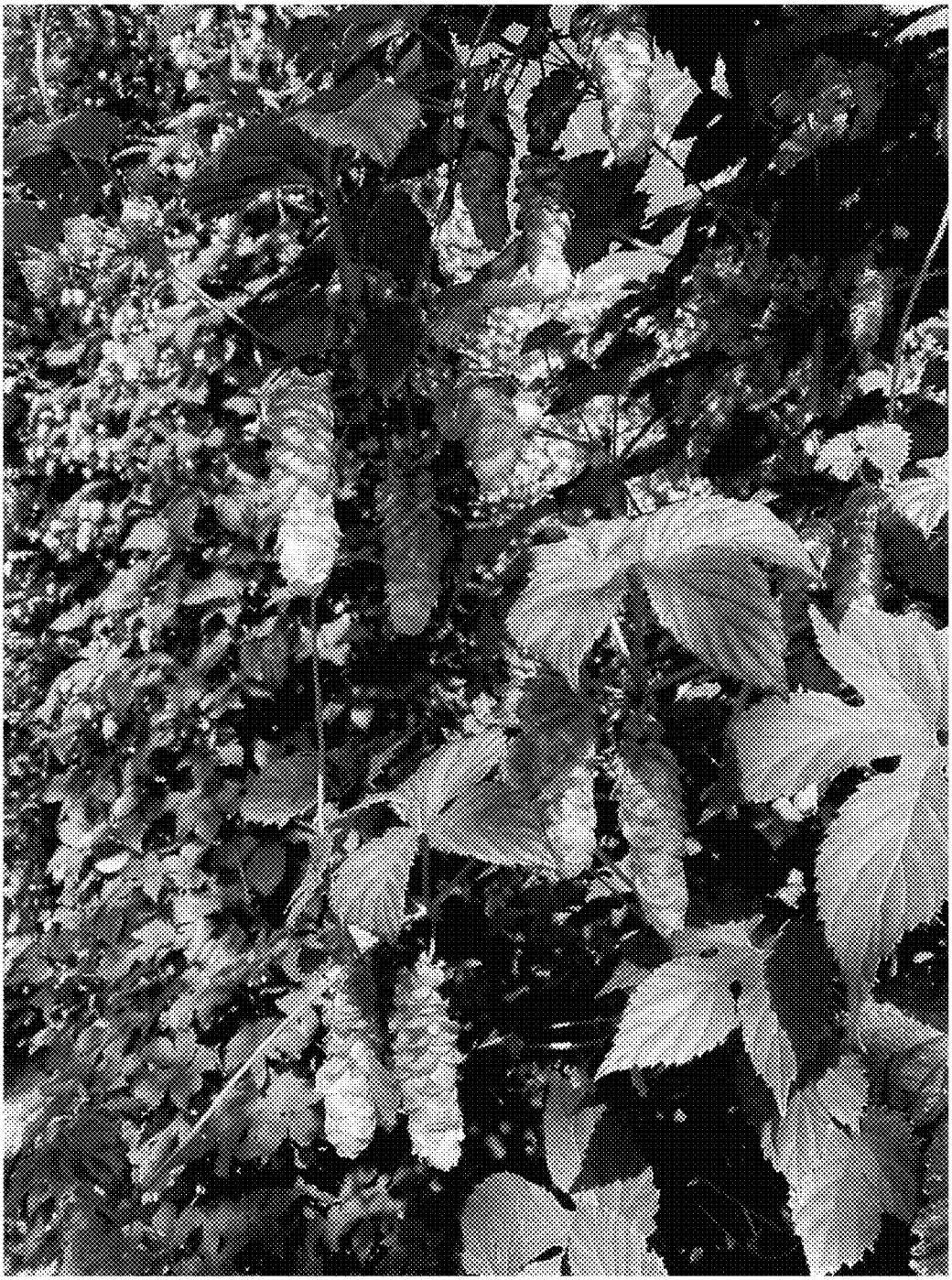
FIG. 2 illustrates a close-up view of a specimen of the 'NZH-2077' plant growing outdoors.
Figure 3:
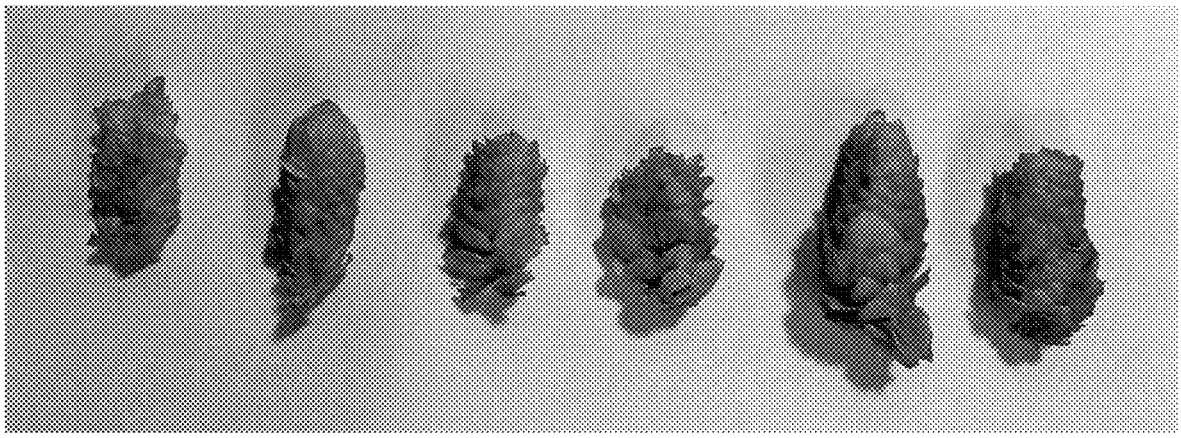
FIG. 3 illustrates specimens of 'NZH-2077' dried cones.

The chart used in the identification of colors is that of The Royal Horticultural Society (The R.H.S. Colour Chart, 2001 edition). The terminology which precedes reference to the chart has been added to indicate the corresponding color in more common terms and The R.H.S. Colour Chart designation herein represents the closest color observed on the majority of the specified botanic features. The description is based on two to three-year-old specimens of the new variety, observed during the 2024-2025 season while growing in Motueka, New Zealand.

Botanical classification: *Humulus lupulus* L. cultivar 'NZH-2077'.

Commercial classification: Hop Plant.

Chemical characteristics:

TABLE 1

| Compound | Percentage |
|---|---|
| Alpha acid | 9.9% |
| Beta acid | 4.7% |
| Cohumulone content (as % of Alpha acids) | 35.3% |
| Humulene | 19% |
| Farnesene | 1.2% |
| humulene caryophyllene ratio | 3.65:1 |

Plant:

*Growth type*.—Normal.

*Shape*.—Cylindrical.

*Volume of head*.—Medium.

*Use*.—Brewing.

*Harvest date*.—Late (commencing mid to late March) in Motueka, New Zealand, under normal conditions.

*Cone yield*.—Average 1.9 tonnes/ha.

Main shoot:

*Anthocyanin coloration*.—Weak, Red-Purple Group 60B.

*Background color of upper half*.—Red-Purple Group 59C.

*Intensity of color*.—Medium.

*Stripe*.—Present.

*Stripe color*.—Red-Purple Group 59C.

*Node pubescence*.—Weak.

*Vine length*.—Approximately 5.0 m.

*Vine diameter*.—At base is approximately 10.04 mm on average; halfway up vine is approximately 9.8 mm on average.

*Internode length*.—Approximately 29.0 cm.

*Thorns*.—Present.

*Number of thorns*.—Very few.

*Anthocyanin coloration of thorns*.—Weak, Green-Yellow Group 1C.

Lateral shoots:

*Side shoot from middle third of plant*.—Length: medium; approximately 61.3 cm on average. — density of foliage: medium. — number of cones per node: medium; approximately 15.6 on average. — number of nodes per lateral shoot: medium; approximately 5.5 on average.

*Side shoot from upper third of plant*.—Length: medium; approximately 61.1 cm on average. — number of cones per node: medium; approximately 16.1 on average. — number of nodes per lateral shoot: medium; approximately 12.5 on average.

*Distribution of lateral shoots*.—Even.

*Attitude of lateral shoots*.—Pendant.

Leaves:

*Size*.—Medium; length is approximately 128.7 mm on average; width is approximately 141.9 mm on average.

*Arrangement*.—Opposite.

*Blistering of upper side of blade*.—Medium.

*Color*.—Upper surface is Green Group 141B.

*Intensity of green color of upper side of blade*.—Medium.

*Glossiness of upper surface*.—Absent or very weak.

*Lobes*.—Present.

*Lobe length*.—Approximately 83.9 mm on average.

*Number of lobes*.—Five.

*Leaf margin*.—Dentate.

*Lateral sinus*.—Open.

*Spines on midrib of under surface*.—Number: few. — shape: straight.

*Venation*.—Palmate.

*Petiole*.—Length: approximately 116.72 mm on average. — width: approximately 4.67 mm on average. — color: Red-Purple Group 63C.

*Stipule*.—Pose: drooping. — size: large; length is approximately 22.39 mm on average; width is approximately 16.4 mm on average. — shape: overall shape is triangular; shape of tip is pointed. — color: Green Group 138D.

Inflorescence:

Flowering:

*Commencement of flowering*.—Medium (December in Motueka, New Zealand).

Cone:

*Length*.—Long; approximately 47.8 mm on average.

*Width*.—Approximately 19.8 mm on average.

*Shape of longitudinal section*.—Narrow ovate.

*Shape of cross section*.—Square.

*Green weight* (*average over* 100).—High with a range of between 151.0 g to 200.0 g.

*Compactness*.—Medium.

*Strig*.—Length: long; approximately 43.6 mm on average. — width: thick; approximately 5.1 mm on average. — number of nodes: many; approximately 19 on average. — anthocyanin: absent. — color: Green Group 138D.

*Bract*.—Frequency: many. — size: large; length is approximately 19.9 mm on average; width is approximately 13.7 mm on average. — ratio width/length: large. — color of upper and lower surfaces: Yellow-Green Group 145C. — intensity of green color: dark. — tip shape: narrowly obtuse. — tip position: oppressed.

*Bracteole*.—Color: Yellow Group 5D. — length: approximately 15.6 mm on average. — width: approximately 8.2 mm on average.

Development:

*Pest and disease*.—'NZH-2077' does not appear particularly resistant or susceptible to pests or diseases known to afflict *Humulus lupulus*.

*Hardiness*.—Zone classification not determined.

The invention claimed is:

1. A new and distinct variety of Hop plant named 'NZH-2077', substantially as illustrated and described herein.

* * * * *